United States Patent [19]

Sebag et al.

[11] Patent Number: 5,364,625
[45] Date of Patent: Nov. 15, 1994

[54] ALKYLTHIOPOLY (ETHYLIMIDAZOLIUM) COMPOUNDS, PROCESS FOR PREPARING THEM AND THEIR USE AS BIOCIDAL AGENTS

[75] Inventors: Henri Sebag; Claude Mahieu, both of Paris, France

[73] Assignee: L'Oreal, Paris, France

[21] Appl. No.: 902,729

[22] Filed: Jun. 23, 1992

[30] Foreign Application Priority Data

Jun. 24, 1991 [FR] France ................... 91 07735

[51] Int. Cl.$^5$ ................... A61K 7/48; A61K 7/04; C07D 233/56
[52] U.S. Cl. ................... 424/401; 424/45; 424/61; 424/70; 424/450; 424/DIG. 1; 424/DIG. 5; 514/844; 514/881; 514/937; 514/944; 514/945; 548/342.1
[58] Field of Search ................... 424/70, 61, 401, 45, 424/450, 47, DIG. 1, DIG. 5; 548/341, 336; 514/844, 881, 937, 944, 945

[56] References Cited

U.S. PATENT DOCUMENTS 3,882,136  5/1975  Levon ................... 260/299

FOREIGN PATENT DOCUMENTS

WO90/04918  5/1990  WIPO .

Primary Examiner—Thurman K. Page
Assistant Examiner—Jyothsna Venkat
Attorney, Agent, or Firm—Jacobson, Price, Holman & Stern

[57] ABSTRACT

The present invention relates to new cationic surfactant compounds of formula:

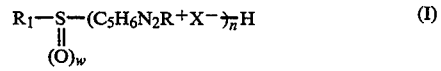

in which:
$R_1$ denotes a $C_{12}$–$C_{18}$ alkyl radical;
R denotes methyl, ethyl, hydroxyethyl or benzyl; X denotes an inorganic or organic anion;
n is between 2 and 15;
w equals 0, 1 or 2;
the group $[C_5H_6N_2R^+]$ representing the following structures, taken mixed or separately:

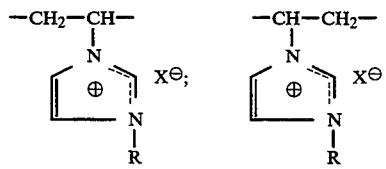

as well as to their use as biocides.

9 Claims, No Drawings

ALKYLTHIOPOLY (ETHYLIMIDAZOLIUM) COMPOUNDS, PROCESS FOR PREPARING THEM AND THEIR USE AS BIOCIDAL AGENTS

The present invention relates to new compounds of the alkylthiopoly(ethylimidazolium) type, to a process for preparing them and to their use as biocidal agents in various technical fields such as cosmetics, human and veterinary pharmacy, agriculture, paints and varnishes and paper-making.

Products having bactericidal and/or fungicidal properties and which are well tolerated by the skin and hair are sought in the field of cosmetics, in particular in anti-dandruff products and in skin cleansing products.

In dermopharmacy, the use of bactericidal and/or fungicidal products is also highly advantageous, in particular in the treatment of diseases affecting the cornified layer of the epidermis of humans or animals, such as acne, or in the treatment of mycoses, or in the treatment of diseases affecting the mucosae.

Cationic compounds of the quaternary ammonium type are commonly used as bactericidal agents in the field of cosmetics or pharmacy. These compounds present, however, problems of tolerance.

Cetyltriethylammonium bromide, better known by the name of "CETAVLON", is known in the prior state of the art.

The Applicant has discovered new compounds derived from imidazole, possessing good biocidal activity as well as lower toxicity compared to the known compounds. They possess, in addition, good cosmetic properties with respect to the hair, the skin and the nails.

These compounds possess, moreover, advantageous surfactant properties.

The subject of the present invention is new cationic compounds of the imidazolium type.

Another subject of the invention consists of a process for preparing these compounds.

The invention also relates to the use of these compounds as biocidal agents in many fields of the chemical industry, and more especially cosmetics and dermopharmacy.

Other subjects will become apparent in the light of the description and the examples which follow.

The compounds according to the present invention correspond to the following formula (I):

$$R_1\text{—S—}(C_5H_6N_2R^+X^-)_{\overline{n}}H \quad \text{(I)}$$
$$\underset{(O)_w}{\|}$$

in which:

$R_1$ denotes a linear or branched alkyl radical having 12 to 18 carbon atoms;

R denotes a methyl, ethyl, hydroxyethyl or benzyl radical;

$X^-$ denotes an inorganic or organic anion; n is between 2 and 15 or represents a statistical value between 2 and 15; w equals 0, 1 or 2; the group $[C_5H_6N_2R^+X^-]$ representing the following structures, taken mixed or separately:

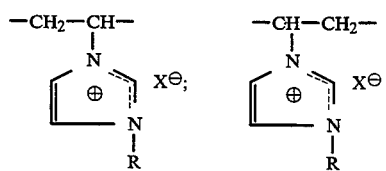

The anions $X^-$ are chosen, in particular, from halides, alkylsulfates, alkylsulfonates and arylsulfonates.

The anion $X^-$ preferably denotes $Cl^-$, $Br^-$, $I^-$, $CH_3SO_3^-$,

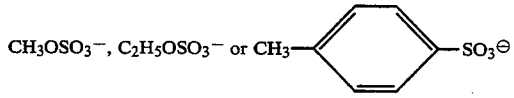

Preferred compounds according to the present invention are chosen from those of formula (I) in which R denotes a methyl radical and $X^-$ the $CH_3OSO_3^-$ anion, and R denotes a benzyl radical and $X^-$ the $Cl^\ominus$ anion.

The compounds according to the invention may be prepared by the free-radical addition of an alkylthio group to one or more molecules of 1-vinylimidazole, to obtain an alkylthiopoly(ethylimidazole) surfactant of formula (II):

$$R_1S(C_5H_6N_2)_{\overline{n}}H \quad \text{(II)}$$

in which $R_1$ has the same meaning as stated above, the group $C_5H_6N_2$ signifying the following structures, taken mixed or separately:

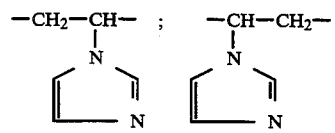

The alkylthiopoly(ethylimidazole) compound thereby obtained is then quaternized by alkylation with a compound of formula RX, in which R and X have the meanings stated above.

In the case where w is equal to 1 or 2, the products thereby obtained are oxidized with hydrogen peroxide, according to a known process, at a temperature of between 20° and 50° C.

The process for preparing the compounds of the invention may be represented by the following reaction scheme:

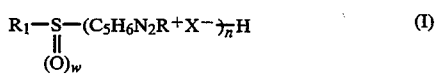

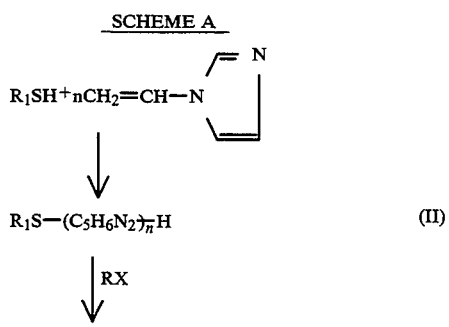

-continued
SCHEME A

  (I)

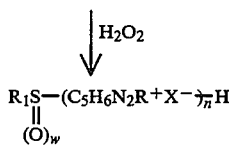

The free-radical reaction takes place in a solvent medium in the presence of a free-radical initiator.

As free-radical initiators, hydroperoxides such as tert-butyl hydroperoxide, peroxides such as dibenzoyl peroxide, peresters such as tert-butyl peroxybenzoate or azo derivatives and especially azobisisobutyronitrile may be mentioned.

The solvents which are usable must be inert with respect to the reactants, and may be chosen from $C_1$–$C_4$-alcohols such as methanol and isopropanol, alkyl ethers, glycol ethers, cyclic ethers such as tetrahydrofuran, and aliphatic or $C_6$–$C_8$ aromatic hydrocarbons such as toluene.

The mercaptan of formula $R_1SH$ is dissolved in the solvent in the presence of 1-vinylimidazole, and the free-radical initiator is then added, the reaction being performed under an inert atmosphere. The compounds of formula (II) thereby obtained are then alkylated with an alkylating agent RX in the presence of an inert solvent such as those mentioned above.

The alkylating agents RX used according to the invention are chosen, for example, from methyl, ethyl or hydroxyethyl halides, methyl or ethyl sulfates, methyl sulfonate or methyl para-toluenesulfonate.

The compounds of formula (II) are new and constitute another subject of the invention.

The alkylthiopoly(ethylimidazolium) compounds of formula (I) of the invention possess good biocidal properties.

Good biocidal activity has been observed according to conventional methods on the following strains: *Pseudomonas aeruginosa, Staphylococcus aureus, Candida albicans*. These strains may be considered as representatives of the main bacteria and fungi responsible for skin complaints of bacterial or mycobacterial origin or those due to the establishment of pathogenic yeasts.

The low toxicity of the compounds of the invention was observed by hemolysis of the red cells in blood samples.

The compounds according to the present invention may be used as biocidal agents or as preservatives in the field of the chemical industry, in particular in cosmetic products, and the pharmaceutical industry in its human or veterinary applications, agricultural products, paints and varnishes and paper-making.

The compounds of formula (I) as defined above have the feature of binding to keratinous substances such as skin, hair and nails.

The compounds of the invention may be used as surfactants.

Their cationic amphiphilic character endows them, in addition, with conditioning properties such as those of disentangling, softness, sheen and suppleness with respect to the hair and properties of softness with respect to the skin.

The compounds of the invention are especially advantageous for the cosmetic care of keratinous substances. They are also especially advantageous for the treatment of skin complaints of bacterial or mycobacterial origin or those due to the establishment of pathogenic yeasts. They may, in particular, be used in pharmaceutical compositions which can be applied topically to the mucosae or to the skin for the treatment of acne or mycoses, or in cosmetic compositions, in particular body deodorants or mouthwashes.

They are also used in hair-care compositions for the suppression of dandruff.

Another subject of the invention hence consists of pharmaceutical or cosmetic compositions for the treatment or care of human keratinous substances, containing an effective amount of compounds of the formula (I) as defined above in a physiologically acceptable medium.

The compounds of formula (I) are present in concentrations preferably of between 0.1 and 10% by weight relative to the total weight of the composition, and preferably 0.2 and 5% by weight.

These compositions can be aqueous, alcoholic or aqueous-alcoholic solutions, or emulsions which take the form of a milk or cream, foam, gel, paste or stick, or alternatively the form of a spray.

These compositions may be pressurized in aerosol devices, in the presence of a propellent agent, optionally in the presence of foam generators or emulsifying agents.

As propellent agent, agents of the freon type, $C_3$–$C_5$ alkanes, chlorinated solvents such as methylene chloride or ethers such as dimethyl ether may be mentioned.

The compositions can also take the form of a vesicular dispersion based on ionic lipids (liposomes) or non-ionic lipids.

These compositions can contain water, a physiologically acceptable solvent or a mixture of water and this solvent, the solvent being chosen from $C_1$–$C_4$ lower alcohols such as ethanol, isopropanol and propanol or polyhydric alcohols such as propylene glycol or glycerol; these solvents being present in proportions of between 0 and 50%.

The compositions according to the invention can also contain oils, natural or synthetic waxes, nonionic, cationic, weakly anionic, amphoteric or zwitterionic dispersant, emulsifying, foaming surfactant products, fatty alcohols, silicones, polymers of natural origin such as cellulose, guar, chitosan derivatives, peptides, synthetic polymers, conditioners, foam stabilizers, thickeners, pearlescent agents, sterols, salts, sun screens, perfumes, colorings, hydrating agents and preservatives other than those of formula (I), in particular those of the isothiazolone family such as 2-methylisothiazolone, 2-octylisothiazolone, 5-chloro-2-methylisothiazolone, benzoisothiazolone or those described in Patent FR-2,492,376.

A preferred form for cosmetic use consists of anti-dandruff lotions or shampoos.

Another subject of the invention consists of a process for the cosmetic treatment of the hair or scalp, wherein a hair-care composition as defined above is applied, and is optionally followed by a rinse with water.

It is observed that the hair thus treated is more supple, more shiny, smoother and easily disentangled.

The applications to which the invention more especially relates are shampoos, hair and scalp treatments for the suppression of dandruff and treatment of the skin for acne and mycoses.

The subject of the present invention is also the use of the compounds of formula (I) for the preparation of a medicinal product intended for the treatment of diseases of bacterial or mycobacterial origin or those due to establishment of pathogenic yeasts.

The examples which follow serve to illustrate the present invention without, however, being limiting in nature.

PREPARATION EXAMPLES

EXAMPLE 1

Preparation of a compound of formula (I) for which $R_1=CH_{12}H_{25}$ $n=2$ $R=CH_3$ $X=CH_3OSO_3^-$, $w=0$

STEP 1

Preparation of a compound of formula (II) for which $R_1=C_{12}H_{25}$ $n=2$

In a 500-ml reactor, 20.24 g (0.1 mol) of dodecanethiol are dissolved at 25° C. in 20 ml of isopropanol.

The solution is placed under a stream of nitrogen, and 28.2 g of 1-vinylimidazole (0.3 mol) are then added in the course of 5 minutes.

Heating is then initiated. When the temperature reaches 50° C., a solution of 1.13 g of azobisisobutyronitrile in 40 ml of isopropanol is added in the course of 45 minutes while the gradual rise in temperature is continued.

When the addition is complete, the reaction medium is maintained at a temperature of 70° C. for 16 hours.

The solvent is then evaporated off under reduced pressure. 48.5 g of a crude product are then obtained.

The member $n=2$ is then separated from this crude product by passage through silica (Merck 60 H—eluent $CH_2Cl_2$ gradually enriched with methanol to attain a 95:5 $CH_2Cl_2/CH_3OH$ mixture).

6 g of the dicondensation product are thereby obtained. The product takes the form of a beige paste.

Base value = 5.10 meq/g (theoretical: 5.12 meq/g).

| ELEMENTAL ANALYSIS | | |
|---|---|---|
| | THEORETICAL | FOUND |
| C | 67.64 | 67.61 |
| H | 9.81 | 9.85 |
| N | 14.34 | 14.40 |
| S | 8.21 | 8.20 |

STEP 2

Quaternization of the compound obtained in Step 1

5.31 g of the compound of Step 1 are solubilized at 25° C. in 2.5 ml of methanol.

When the solution is homogeneous, 3.41 g of dimethyl sulfate are added dropwise in the course of 45 minutes while preventing the temperature from exceeding 50° C.

The mixture is then stirred for 14 h at 25° C.

The solvent is then evaporated off under reduced pressure. An orange-colored amorphous product which is soluble in water is obtained.

| ELEMENTAL ANALYSIS | | |
|---|---|---|
| | THEORETICAL | FOUND |
| C | 48.57 | 48.04 |
| H | 7.84 | 7.89 |
| N | 8.72 | 8.58 |
| O | 19.91 | 21.21 |
| S | 14.96 | 14.77 |

EXAMPLE 2

Preparation of a compound of formula (I) for which $R_1=C_{12}H_{25}$ $n=3$ $R=CH_3$ $X=CH_3OSO_3^-$, $w=0$

STEP 1

Preparation of a compound of formula (II) for which $R_1=C_{12}H_{25}$ $\bar{n}=3$ This compound is prepared according to the procedure of Example 1 (1st step).

The crude product obtained is a mixture of compounds for which n represents an average statistical value of 3.

Base value = 5.74 meq/g (theoretical: 6.21 meq/g)

STEP 2

Quaternization of the compound obtained in the first step

The procedure is similar to that of Example 1 (Step 2), using:

10 g of the compound obtained in the 1st step of Example 3, solubilized in 30 ml of methanol 7.24 g of dimethyl sulfate 17.2 g of an amorphous orange-colored product which is soluble in water are obtained.

| ELEMENTAL ANALYSIS | | |
|---|---|---|
| | THEORETICAL | FOUND |
| C | 45.95 | 44.50 |
| H | 7.24 | 7.32 |
| N | 9.74 | 9.31 |
| O | 22.24 | 24.15 |
| S | 14.86 | 14.60 |

EXAMPLE 3

Preparation of a compound of formula (I) for which $R_1=C_{18}H_{37}$ $\bar{n}=3$ $R=CH_3$ $X=CH_3OSO_3^-$, $w=0$

STEP 1

Preparation of a compound of formula (II) for which $R_1=C_{18}H_{37}$ $\bar{n}=3$ The procedure is similar to that of Example 2 (Step 1) using:

28.66 g of octadecanethiol (0.1 mol) dissolved in 50 ml of isopropanol 28.23 g (0 3 mol) of 1-vinylimidazole 1.13 g of azobisisohutyronitrile in 40 ml of isopropanol.

56.9 g of a beige paste whose base value is 4.20 meq/g are obtained.

STEP 2

Quaternization of the compound obtained in the first step

The procedure is similar to that of Example 2 (Step 2), using:

20 g of the compound obtained in Step 1 dissolved in 100 ml of methanol 10.58 g of dimethyl sulfate 30.60 g of an orange-colored solid whose melting point is 230° C. with decomposition are obtained.

| ELEMENTAL ANALYSIS | | |
|---|---|---|
| | THEORETICAL | FOUND |
| C | 49.45 | 48.64 |
| H | 7.87 | 7.97 |
| N | 8.87 | 8.60 |
| O | 20.27 | 21.67 |
| S | 13.54 | 13.30 |

EXAMPLE 4

Preparation of a compound of formula (I) for which $R_1=C_{12}H_{25}$ $\bar{n}=5$ $R=CH_3$ $X=CH_3OSO_3^-$, $w=0$

STEP 1

Preparation of a compound of formula (II) for which $R_1=C_{12}H_{25}$ and $\bar{n}=5$ (dodecanethiol thioetherified with five 1-ethylimidazole units) (statistical)

The procedure is similar to that of Example 2 (Step 1), using:

20.25 g of dodecanethiol (0.1 mol) dissolved in 20 ml of isopropanol 47 g of 1-vinylimidazole (0.5 mol)

1.88 g of azobisisobutyronitrile in 100 ml of isopropanol.

65 g of a beige paste whose base value is 6.21 meq/g (theoretical: 7.44 meq/g) are obtained.

STEP 2

Quaternization of the compound obtained in the first step

Dodecanethiol thioetherified with five 1-ethyl-3-methylimidazolinium methylsulfate units (statistical)

The procedure is identical to that of Example 2 (Step 2), using:

20 g of the compound of Step 1 dissolved in 100 ml of methanol 15.62 g of dimethyl sulfate.

34 g of an orange-colored solid are obtained.

M.p.=230° C. (decomposition).

EXAMPLE 5

Preparation of a compound of formula (I) for which $R_1=C_{12}H_{25}$ $\bar{n}=10$ $R=CH_3$ $X^-=CH_3OSO_3^-$, $w=0$

STEP 1

Preparation of a compound of formula (II) for which $R_1=C_{12}H_{25}$ and $\bar{n}=10$ (dodecanethiol thioetherified with ten 1-ethylimidazole units) (statistical)

The procedure is similar to that of Example 2 (Step 1), using:

10.2 g of dodecanethiol (0 05 mol) dissolved in ml of isopropanol 47 g of 1-vinylimidazole (0.5 mol)

1.88 g of azobisisobutyronitrile in 100 ml of isopropanol.

The crude product obtained takes the form of a beige paste whose base value is 6.31 meq/g (theoretical: 8.75 meq/g).

STEP 2

Quaternization of the compound obtained in the first step

Dodecanethiol thioetherified with ten 1-ethyl-3-methylimidazolinium methylsulfate units (statistical)

The procedure is identical to that of Example 2 (Step 2), using:

20.6 g of the compound of Step 1 dissolved in 100 ml of methanol 16.38 g of dimethyl sulfate.

35 g of an orange-colored solid are obtained.

M.p.=240° C. (decomposition).

| ELEMENTAL ANALYSIS | | |
|---|---|---|
| | THEORETICAL | FOUND |
| C | 40.95 | 39.09 |
| H | 6.12 | 6.79 |
| N | 11.65 | 10.47 |
| O | 26.61 | 28.59 |
| S | 14.67 | 13.82 |

EXAMPLE 6

Preparation of a compound of formula (I) for which $R_1=C_{18}H_{37}$ $\bar{n}=8$ $R=CH_3$ $X^-=CH_3OSO_3^-$, $w=0$

STEP 1

Preparation of a compound of formula (II) for which $R_1=C_{18}H_{37}$ and $\bar{n}=8$ (octadecanethiol thioetherified with eight 1-ethylimidazole units) (statistical)

In a 500-ml reactor, 14.34 g of octadecanethiol are dissolved at 70° C. and under a stream of nitrogen in 100 ml of isopropanol. The temperature is brought to 40° C., and 37.6 g of 1-vinylimidazole (0.4 mol) are added dropwise in the course of 10 minutes. When the addition is complete, heating is resumed. When the temperature in the reactor reaches 50° C., a solution of 1.50 g of azobisisobutyronitrile in 50 ml of methanol is added in the course of 45 minutes while the gradual rise in temperature is continued. When the addition is complete, the reaction medium is maintained at a temperature of 70° C. for 16 hours. The solvents are then driven off under reduced pressure and 52 g of a pale yellow solid are obtained.

Base value: 6.82 meq/g (theoretical: 7.70 meq/g)

| ELEMENTAL ANALYSIS | | |
|---|---|---|
| | THEORETICAL | FOUND |
| C | 67.02 | 66.10 |
| H | 8.34 | 8.77 |
| N | 21.56 | 20.26 |
| S | 3.08 | 3.15 |

STEP 2

Quaternization of the compound obtained in the first step

Octadecanethiol thioetherified with eight 1-ethyl-3-methylimidazolium methylsulfate units (statistical)

The procedure is identical to that of Example 2 (Step 2), using:

20 g of the compound of Step 1 dissolved in 100 ml of methanol
17.19 g of dimethyl sulfate.
36.5 g of an orange-colored solid are obtained.

| | ELEMENTAL ANALYSIS | |
|---|---|---|
| | THEORETICAL | FOUND |
| C | 43.39 | 42.95 |
| H | 6.59 | 6.74 |
| N | 10.94 | 10.70 |
| O | 25.00 | 26.06 |
| S | 14.09 | 13.89 |

EXAMPLE 7

Preparation of a compound of formula (I) for which $R_1=C_{18}H_{37}$ $\bar{n}=10$ $R=CH_3$ $X^-=CH_3OSO_3^-$, $w=0$

STEP 1

Preparation of a compound of formula (II) for which $R_1=C_{18}H_{37}$ and $\bar{n}=10$ (octadecanethiol thioetherified with ten 1-ethylimidazole units) (statistical)

The procedure is similar to that of Example 6 (Step 1), using:
14.37 g of octadecanethiol (0.05 mol) dissolved in 100 ml of isopropanol
47 g of 1-vinylimidazole (0.5 mol)
1.88 g of azobisisobutyronitrile in 50 ml of methanol.
61 g of a pale yellow solid whose base value is 6.98 meq/g (theoretical: 8.15 meq/g) are obtained.

| | ELEMENTAL ANALYSIS | |
|---|---|---|
| | THEORETICAL | FOUND |
| C | 66.52 | 66.29 |
| H | 8.05 | 8.93 |
| N | 22.82 | 19.66 |
| S | 2.61 | 2.62 |

STEP 2

Quaternization of the compound obtained in the first step

Octadecanethiol thioetherified with ten 1-ethyl-3-methylimidazolium methylsulfate units (statistical)

The procedure is identical to that of Example 2 (Step 2), using:
20 g of the compound obtained in Step 1 dissolved in 100 ml of methanol
17.39 g of dimethyl sulfate.
36.5 g of an orange-colored solid are obtained.

| | ELEMENTAL ANALYSIS | |
|---|---|---|
| | THEORETICAL | FOUND |
| C | 42.46 | 42.60 |
| H | 6.40 | 4.46 |
| N | 11.26 | 11.13 |
| O | 25.71 | 27.02 |
| S | 14.17 | 13.15 |

EXAMPLE 8

Preparation of a compound of formula (I) for which $R_1=C_{18}H_{37}$ $\bar{n}=12$ $R=CH_3$ $X^-=CH_3OSO_3^-$, $w=0$

STEP 1

Preparation of a compound of formula (II) for which $R_1=C_{18}H_{37}$ and $\bar{n}=12$ (octadecanethiol thioetherified with twelve 1-ethylimidazole units) (statistical)

The procedure is similar to that of Example 6 (Step 1), using:
14.37 g of octadecanethiol (0.05 mol) dissolved in 100 ml of isopropanol
56.4 g of 1-vinylimidazole (0.6 mol)
2.16 g of azobisisobutyronitrile in 60 ml of methanol.
70 g of a yellow solid whose base value is 7.35 meq/g (theoretical: 8.48 meq/g) are obtained.

| | ELEMENTAL ANALYSIS | |
|---|---|---|
| | THEORETICAL | FOUND |
| C | 66.16 | 66.45 |
| H | 7.83 | 9.08 |
| N | 23.74 | 19.92 |
| S | 2.26 | 2.29 |

STEP 2

Quaternization of the compound obtained in the first step

Octadecanethiol thioetherified with twelve 1-ethyl-3-methylimidazolium methylsulfate units (statistical)

The procedure is identical to that of Example 2 (Step 2), using:
20 g of the compound obtained in Step 1 dissolved in 100 ml of methanol
18.2 g of dimethyl sulfate.
36.1 g of an orange-colored solid are obtained.

| | ELEMENTAL ANALYSIS | |
|---|---|---|
| | THEORETICAL | FOUND |
| C | 41.82 | 42.42 |
| H | 6.26 | 6.37 |
| N | 11.48 | 11.62 |
| O | 26.21 | 27.08 |
| S | 14.23 | 13.08 |

EXAMPLE 9

Preparation of a compound of formula (I) for which $R_1=C_{12}H_{25}$ $\bar{n}=10$ $R=$benzyl $X^-=Cl^-$ $w=0$

STEP 1

29 g of the compound obtained in Step 1 of Example 5 are solubilized in 100 ml of dimethylacetamide at 80° C. 63.85 g of benzyl chloride (0.50 mol) are added at 80° C. in the course of 15 minutes.

The mixture is then heated to 80° C. for 24 hours and thereafter brought back to 25° C. The product is precipitated with stirring in 850 ml of tetrahydrofuran.

The precipitate is filtered off, rinsed with twice 300 ml of tetrahydrofuran and dried. The precipitate, which is hygroscopic, is taken up with 600 ml of water and the final traces of tetrahydrofuran are removed in a rotary evaporator.

The solution, chilled in a bath of ethanol and dry ice, is then lyophilized. 29 g of a beige powder having a water content of approximately 9% are obtained.

| ELEMENTAL ANALYSIS | | |
|---|---|---|
| | CALCULATED (with 9% water) | FOUND |
| C | 60.03 | 59.33 |
| H | 6.93 | 7.07 |
| N | 10.61 | 10.16 |
| O | 7.78 | 7.21 |
| S | 1.11 | 0.96 |
| Cl | 13.63 | 14.17 |

COMPOSITION EXAMPLES

EXAMPLE 1

OIL-IN-WATER EMULSION CREAM

| | | |
|---|---|---|
| — | Cetyl alcohol | 5.0 g |
| — | Glyceryl distearate | 1.5 g |
| — | Glyceryl monostearate | 1.5 g |
| — | Polyethylene glycol stearate containing 50 mol of ethylene oxide, sold by the company ICI under the name MYRJ 53 | 3.0 g |
| — | Jojoba oil | 3.0 g |
| — | Liquid paraffin | 3.0 g |
| — | 2-Ethylhexyl para-methoxycinnamate sold by the company GIVAUDAN under the name PARSOL MCX | 1.0 g |
| — | 2-Hydroxy-4-methoxybenzophenone sold by the company BASF under the name UVINUL M40 | 1.0 g |
| — | Perfumes, preservative qs | |
| — | Compound of Example 2 | 1.0 g |
| — | Demineralized water qs | 100.0 g |

The fats and the emulsifiers are heated to about 80°–85° C. Separately, the water containing the compound of Example 2 is heated to 80°–85° C., and the fatty phase is added to the aqueous phase. After 10 minutes of brisk stirring, the preparation is allowed to cool with moderate stirring and the perfume and preservatives are then added

EXAMPLE 2

OIL-IN-WATER EMULSION CREAM

| | | |
|---|---|---|
| — | Triethanolamine | 1.3 g |
| — | Palm oil | 3.0 g |
| — | Mixture of cetyl/stearyl 2-ethylhexanoate and isopropyl myristate (90:10) | 3.0 g |
| — | Hydrogenated isoparaffin | 10.0 g |
| — | Stearic acid | 2.0 g |
| — | Cetyl/stearyl alcohol | 1.5 g |
| — | Isopropyl myristate | 3.0 g |
| — | Crosslinked polyacrylic acid sold by the company GOODRICH under the name CARBOPOL 940 | 0.6 g |
| — | Polyethylene glycol monostearate (containing 50 mol of ethylene oxide, sold by the company ICI under the name MYRJ 53 | 3.0 g |
| — | Mixture of glyceryl stearate and polyethylene glycol stearate (containing 10 mol of ethylene oxide) (50:50), sold by the company ICI under the name ARLACEL 165 | 3.0 g |
| — | Mixture of cetyl/stearyl alcohol and oxyethylenated cetyl/stearyl alcohol containing 33 mol of ethylene oxide, sold by the company HENKEL under the name SINNOWAX AO | 3.0 g |
| — | 2-Ethylhexyl para-methoxycinnamate sold by the company GIVAUDAN under the name PARSOL MCX | 1.0 g |
| — | 2-Hydroxy-4-methoxybenzophenone sold by the company BASF under the name UVINUL M 40 | 1.0 g |
| — | Perfumes, preservatives qs | |
| — | Compound of Example 2 | 1.0 g |
| — | Demineralized water qs | 100.0 g |

This emulsion as in Example 1.

EXAMPLE 3

SHAMPOO

| | | |
|---|---|---|
| — | Weakly anionic surfactant of formula: $C_{12}H_{25}(OCH_2CH_2)_nOCH_2COOH$ in which n = 4, in 95% solution, sold by the company CHEMY under the name AKYPO RLM 45 and prepared at a concentration of 20% of AS, neutralized with sodium hydroxide to pH 7 | 10.0 g AS |
| — | Sodium cocoamidoethyl(N-hydroxyethyl-N-carboxymethyl)glycinate sold by the company MIRANOL under the name MIRANOL C2M concentrate NP | 1.3 g |
| — | Compound of Example 5 | 0.1 g |
| — | Water qs | 100.0 g |
| — | Natural pH = 7.5 | |

EXAMPLE 4

SHAMPOO

| | | |
|---|---|---|
| — | Sodium cocoamidoethyl(N-hydroxyethyl-N-carboxymethyl)glycinate sold by the company MIRANOL under the name MIRANOL C2M concentrate NP | 20.0 g |
| — | Compound of Example 7 | 0.1 g |
| — | Water qs | 100.0 g |
| — | Natural pH = 8 | |

EXAMPLE 5

OIL-IN-WATER EMULSION CREAM

| | | |
|---|---|---|
| — | Cetyl alcohol | 5.0 g |
| — | Glyceryl distearate | 1.5 g |
| — | Glyceryl monostearate | 1.5 g |
| — | Polyethylene glycol stearate containing 50 mol of ethylene oxide, sold by the company ICI under the name MYRJ 53 | 3.0 g |
| — | Jojoba oil | 3.0 g |
| — | Liquid paraffin | 3.0 g |
| — | 2-Ethylhexyl para-methoxycinnamate sold by the company GIVAUDAN under the name PARSOL MCX | 1.0 g |
| — | 2-Hydroxy-4-methoxybenzophenone sold by the company BASF under the name UVINUL M40 | 1.0 g |
| — | Perfumes, preservative qs | |
| — | Compound of Example 9 | 1.0 g |
| — | Demineralized water qs | 100.0 g |

The fats and the emulsifiers are heated to about 80°–85° C. Separately, the water containing the compound of Example 9 is heated to 80°–85° C., and the fatty phase is added to the aqueous phase. After 10 minutes of brisk stirring, the preparation is allowed to cool with moderate stirring and the perfume and preservatives are then added.

EXAMPLE 6

Face care cream for greasy skin

The following products are mixed by melting at a temperature of 110° C.:

Nonionic lipid of formula:

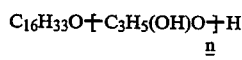

in which formula $\bar{n}$ is an average statistical value equal to 3 and in which formula —$C_3H_5(OH)O$— is represented by the following structures, taken mixed or separately:

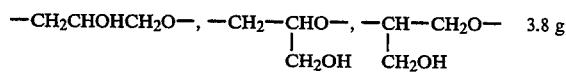 3.8 g

| | |
|---|---|
| Cholesterol | 3.8 g |
| Monosodium stearoylglutamate sold by the company AJINOMOTO under the name "ACYLGLUTAMATE HS 11" | 0.4 g |

The temperature of the molten mixture is then brought down to 90° C. A mixture consisting of 60.6 g of water, 3 g of glycerol and 1 g of the compound of Example 3 is added gradually at a temperature of 70° C. The mixture is homogenized using a VIRTIS ultradisperser for 6 minutes at a speed of 40,000 rpm. A dispersion of lipid vesicles whose average size is 230 nm is thereby obtained. 1 g of water containing 0.15 g of diazolidinylurea, sold by the company SUTTON under the name "GERMAL II", and 0.05 g of ethylenediaminetetraacetic acid dipotassium salt are then added.

The following are then added:

10 g of decamethylcyclopentasiloxane sold by RHONE POULENC under the name "SILBIONE Huile 700 45 V5"

0.8 g of dimethicone sold by RHONE POULENC under the name "SILBIONE 747 V 300"

0.01 g of propyl para-hydroxybenzoate

The whole is subjected to the action of the VIRTIS disperser for 4 minutes at 40,000 rpm.

The following are added:

0.42 g of crosslinked polyacrylic acid sold by the company GOODRICH under the name "CARBOPOL 940"

0.2 g of methyl para-hydroxybenzoate 14 g of water 0.7 g of triethanolamine.

A thick white cream is thereby obtained.

We claim:

1. A compound of the formula (I):

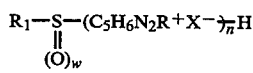 (I)

in which:

$R_1$ denotes a linear or branched alkyl radical having 12 to 18 carbon atoms;

R denotes a methyl, ethyl, hydroxyethyl or benzyl radical;

$X^-$ denotes an inorganic or organic anion;

n is between 2 and 15 or represents a statistical value between 2 and 15;

w equals 0, 1 or 2;

the group ($C_5H_6N_2R^+$) representing the following structures, taken together or separately:

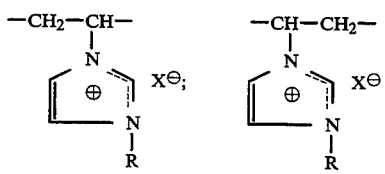

2. A compound as claimed in claim 1, wherein $X^-$ is a member selected from the group consisting of $Cl^-$, $Br^-$, $I^-$, $CH_3OSO_3^-$, $C_2H_5OSO_3^-$, $CH_3SO_3^-$, and

3. A compound as claimed in claim 1, wherein the radical R denotes methyl and $X^-$ represents $CH_3OSO_3^-$, or R denotes benzyl and $X^-$ denotes $Cl^-$.

4. A composition for the care or treatment of human keratinous substances comprising the hair, skin, nails and mucosae, which contains an effective amount of at least one compound of formula (I) as claimed in claim 1 in a physiologically acceptable medium.

5. The composition as claimed in claim 4, which contains the compound of formula (I) in concentrations of between 0.1 and 10% by weight relative to the total weight of the composition.

6. The composition as claimed in claim 4, which is in the form selected from the group consisting of aqueous solutions, aqueous-alcoholic solutions, alcoholic solution, milk, cream, foam, gel, paste, stick, spray, vesicular dispersion and aerosol.

7. The composition as claimed in claim 4 which contains water, a mixture of water and solvent(s), or a solvent, the solvent being selected from the group consisting of $C_1$–$C_4$ monohydric alcohols and polyhydric alcohols, and the solvent being present in proportions of between 0 and 50%.

8. The composition as claimed in claim 4, further comprising at least one member selected from the group consisting of oils, natural waxes, synthetic waxes, fatty alcohols, silicones, nonionic, cationic, weakly anionic, amphoteric surfactants, zwitterionic surfactants, polymers of natural origin, synthetic polymers, conditioners, foam stabilizers, thickeners, pearlescent agents, sterols, sun screens, preservatives other than those of formula (I), perfumes, colorings, and hydrating agents.

9. A pharmaceutical composition suitable for topical application to the skin for the treatment of skin diseases, which consists of a composition as defined according to claim 4.

* * * * *